United States Patent [19]

Schweighardt et al.

[11] Patent Number: 5,196,348
[45] Date of Patent: * Mar. 23, 1993

[54] PERFLUORO-CROWN ETHERS IN FLUORINE MAGNETIC RESONANCE SPECTROSCOPY OF BIOPSIED TISSUE

[75] Inventors: Frank K. Schweighardt, Allentown; Joseph A. Rubertone, Coatesville, both of Pa.

[73] Assignee: Air Products and Chemicals, Inc., Allentown, Pa.

[*] Notice: The portion of the term of this patent subsequent to Jun. 13, 2006 has been disclaimed.

[21] Appl. No.: 725,692

[22] Filed: Jul. 3, 1991

Related U.S. Application Data

[62] Division of Ser. No. 535,818, Jun. 11, 1990, Pat. No. 5,068,098.

[51] Int. Cl.$^5$ .............. G01N 24/00; G01N 31/00; A61K 31/335
[52] U.S. Cl. ..................... 436/173; 424/9; 128/653.4; 514/450; 514/832
[58] Field of Search .............. 424/9; 436/173; 128/653.4; 514/450, 832

[56] References Cited

U.S. PATENT DOCUMENTS

| | | | |
|---|---|---|---|
| 4,523,039 | 6/1985 | Lagow et al. | 568/615 |
| 4,570,004 | 2/1986 | Lagow et al. | 549/352 |
| 4,639,364 | 1/1987 | Hoey | 424/9 |
| 4,838,274 | 6/1989 | Schweighardt et al. | 128/654 |
| 5,068,098 | 11/1991 | Schweighardt et al. | 424/9 |
| 5,070,213 | 12/1991 | Huang et al. | 549/448 |

FOREIGN PATENT DOCUMENTS 0118281 12/1984 European Pat. Off. .

OTHER PUBLICATIONS

Bottomley, Pa., Computerized Radiology 8(2):57-77 (1984).
Nature, vol. 242, pp. 190-191, 1973 Lauterbur, PC.
Damadian, Science, vol. 171, p. 1151, 1971 Tumor Detection by Nuclear Magnetic Resonance.
Mattrey, R. F.; "Perfluorocarbon Compounds:Applications in Diagnostic Imaging"; SPIE; vol. 626, Medicine, XIV/Pacs IV (1986), pp. 18-23.
Longmaid, III et al.; "In vivo $^{19}$F NMR Imaging of Liver, Tumor and Abscess in Rats"; Investigative Radiology; Mar./Apr. 1985; vol. 20; pp. 141-144.
Patronas et al; "Brain-tumor Imaging Using Radiopaque Perfluorocarbon"; Journal of Neurosurgery; May 1983; vol. 58; pp. 650-653.
Mattrey, R. F. et al; "Perfluorochemicals as US Contrast Agents for Tumor Imaging and Hepatosplenography:Preliminary Clinical Results"; Radiology; May 1987; vol. 163; No. 2. pp. 339-343.
Parhami & Fung; "Fluorine-19 Relaxation Study of Perfluoro Chemicals as Oxygen Carriers"; J. Physical Chemicals; 1983; pp. 1928-1931.
Nunnally, et al; "Fluonine-19 ($^{19}$F) NMR in Vivo:Potential for Flow and Perfusion Measurements"; Proceedings of the Society and Magnetic Resonance in Medicine; 2nd Annual Meet.; Aug. 16-19; pp. 226.
Reid, et al; "The Influence of Oxygenation on the $^{19}$F Relaxation Rates in Flusol-da"; Phys. Med. Biol; vol. 30; No. 7; pp. 677-686 (1985).
Wyrwics et al; "Observations of Fluorinated Anesthetics in Rabbit Brain by $^{19}$F NMR"; Proceedings of the Soc. of Magnetic Resonance in Med; 2nd Annual Meet; Aug. 16-19; (1983); pp. 381-382.
Clark et al; "Perfluorinated Organic Liquids and Emulsions as Biocompatible NMR Imaging Agents for $^{19}$F and Dissolved Oxygen"; Adv. Exp. Med. Biol.; vol. 180(6); pp. 835-845; 1984.

Primary Examiner—Glennon H. Hollrah
Assistant Examiner—Gary E. Hollinden
Attorney, Agent, or Firm—Geoffrey L. Chase; James C. Simmons; William F. Marsh

[57] ABSTRACT

A method is disclosed for nuclear magnetic resonance spectroscopy wherein the improvement is the use of perfluoro 15-crown-5 ether which has 20 magnetically similar fluorine providing a superior signal to noise ratio with resultant enhanced diagnostic resolution.

4 Claims, 4 Drawing Sheets

19F-NMR PERFLUORODECALIN

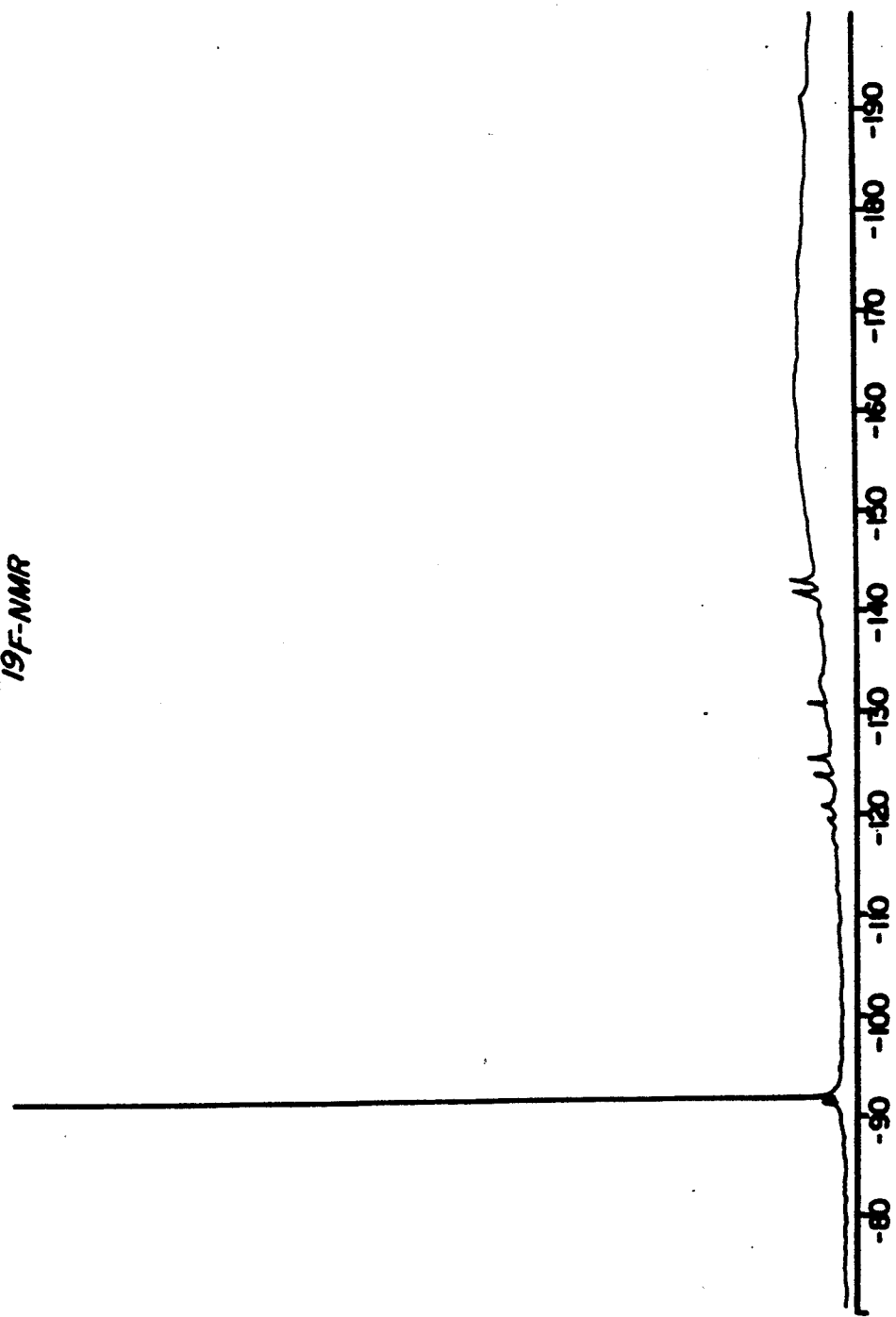

PERFLUORO-CROWN ETHERS IN FLUORINE MAGNETIC RESONANCE SPECTROSCOPY OF BIOPSIED TISSUE

This is a division, of application Ser. No. 07/535,818 filed Jun. 11, 1990 now U.S. Pat. No. 5,068,098.

TECHNICAL FIELD

The present invention is directed to magnetic resonance spectroscopy, also referred to as nuclear magnetic resonance spectroscopy. More particularly, the present invention is directed to methods and compositions for improving magnetic resonance spectra of body organs and tissues using fluorochemicals having unexpectedly enhanced signal to noise response ratios and having an unexpectedly high and diagnostically useful NMR signal response to the presence of oxygen.

BACKGROUND OF THE PRIOR ART

The recently developed techniques of MRI (magnetic resonance imaging) or NMR (nuclear magnetic resonance) imaging encompasses the detection of certain atomic nuclei utilizing magnetic fields and radiofrequency radiation. It is similar in some respects to X-ray computed tomography (CT) in providing a cross-sectional display of the body organ anatomy with excellent resolution of soft tissue detail. In current use, the images produced constitute a map of the distribution density of protons and/or their relaxation times in organs and tissues. The MRI technique is advantageously non-invasive as it avoids the use of ionizing radiation.

While the phenomenon of NMR was discovered in 1945, it is only respectively recently that it has found application as a means of mapping the internal structure of the body as a result of the original suggestion of Lauterbur (Nature, 242, 190–191, 1973). The lack of any known hazard associated with the level of the magnetic and radio-frequency fields that are employed renders it possible to make repeated scans on vulnerable individuals. Additionally, any scan plane can readily be selected including transverse, coronal, and sagittal sections.

In an NMR experiment, the nuclei under study in a sample (e.g. protons) are irradiated with the appropriate radio-frequency (RF) energy in a highly uniform magnetic field. These nuclei, as they relax, subsequently emit RF radiation at a sharp resonant frequency. The emitted frequency (RF) of the nuclei depends on the applied magnetic field.

According to known principles, nuclei with appropriate spin when placed in an applied magnetic field [$B$, expressed generally in units of gauss or tesla ($10<4>$-gauss)] align in the direction of the field. In the case of fluorine, these nuclei precess at a frequency $f=94.08$ MHz at a field strength of 2.35 Tesla. At this frequency, an RF pulse of radiation will excite the nuclei and can be considered to tip the nuclei out of the field direction, the extent of this rotation being determined by the pulse duration and energy. After the RF pulse, the nuclei "relax" or return to equilibrium with the magnetic field, emitting radiation at the resonant frequency. The decay of the signal is characterized by two relaxation times, i.e., $T1$, the spin-lattice relaxation time or longitudinal relaxation time, that is, time taken by the nuclei to return to equilibrium along the direction of the externally applied magnetic field, and $T2$, the spin-spin relaxation time associated with the dephasing of the initially coherent precession of individual proton spins. These relaxation times have been established for various fluids, organs and tissues in different species of mammals.

In MRI, scanning planes and slice thickness can be selected without loss of resolution. This permits high quality transverse, coronal and sagittal images to be obtained directly. The absence of any moving parts in MRI equipment promotes a high reliability. It is believed that MRI or NMR imaging has a greater potential than CT for the selective examination of tissue characteristics in view of the fact that in CT, X-ray attenuation coefficients alone determine image contrast, whereas at least four separate variables ($T1$, $T2$, nuclear spin density and flow) may contribute to the NMR signal. For example, it has been shown (Damadian, Science, Vol. 171, p. 1151, 1971) that the values of the $T1$ and $T2$ relaxation in tissues are generally longer by about a factor of 2 in excised specimens of neoplastic tissue compared with the host tissue.

By reason of its sensitivity to subtle physio-chemical differences between organs and/or tissues, it is believed that MRI may be capable of differentiating tissue types and in detecting diseases which induce physicochemical changes that may not be detected by X-ray or CT which are only sensitive to differences in the electron density of tissue. The images obtainable by MRI techniques also enable the physician to detect structures smaller than those detectable by CT and thereby provide comparable or better spatial resolution.

The use of perfluorocarbon compounds in various diagnostic imaging technologies such as ultrasound, magnetic resonance, radiography and computed tomography, has been set forth in an article by Robert F. Mattrey in SPIE, Volume 626, Medicine, XIV/PACS IV (1986), pages 18–23.

Magnetic resonance imaging of liver tumor and rats using perfluorochemcial emulsions was reported in "In Vivo $^{19}F$ NMR Imaging of Liver, Tumor and Abcess in Rats", H. E. Longmaid III, et al., INVESTIGATIVE RADIOLOGY, March –April 1985, Vol. 20, p. 141–144. The compounds utilized displayed multiple peak NMR spectra.

Imaging of brain tumors with perfluorooctyl bromide has been described in "Brain-Tumor Imaging Using Radiopaque Perfluorocarbon", Nicholas J. Patronas, M.D., et al. JOURNAL OF NEUROSURGERY, May 1983, Vol. 58, pp. 650–653.

Ultrasound imaging of organs has been enhanced by FLUOSOL-DA (perfluorodecalin and perfluorotripropylamine) as reported in "Perfluorochemicals as U. Contrast Agents for Tumor Imaging and Hepatosplenography: Preliminary Clinical Results", Robert F. Mattrey, M.D., et al., RADIOLOGY, May 1987, Vol. 163, No. 2, pp. 339–343.

In European published Patent Application 0 118 281, published Sep. 12, 1984, a technique for the detection of gas in an animal is set forth using nuclear magnetic resonance techniques embodying various fluorochemical agents. Among the fluorochemical agents there is included perfluoro ether polymer (Fomblin Y/01).

In U.S. Pat. No. 4,523,039 the production of fluorocarbon ethers of various structures is set forth wherein the resulting fluorocarbon ether produces a noncyclic structure.

U.S. Pat. No. 4,570,004 describes a method of production and a composition of matter including perfluoro 15-crown-5 ether. The patent identifies that the crown ethers in general can be useful as oxygen carriers and various biomedical products.

U.S. Pat. No. 4,639,364 discloses the use of various fluorine-containing compounds for magnetic resonance imaging.

In parallel to the progress that has been made in the use of Magnetic Resonance Imaging (MRI) as a clinical tool, in vivo NMR spectroscopy (also called magnetic resonance spectroscopy, or MRS), has been developed to probe human body chemistry noninvasively. Efforts are being made to correlate the changes that are observed in an NMR spectrum, such as the changes in chemical shifts and areas of resonance peaks, to biochemical and metabolical states of diseased organs. For example, knowledge of the concentrations of high energy metabolites, such as adenosine triphosphate (ATP), adenosine diphosphate (ADP), phosphocreatine ($PC_r$), and inorganic phosphate (Pi) derived from phosphorous ($^{31}P$) NMR, can be used to determine whether or not a tissue is ischemic. It is also known that tumors do affect the cell metabolism. By monitoring the changes in the spectral features of the tumor, due to the radiation treatments, it is possible to observe a patient's progress without performing repeated biopsies. Progress has also been made in monitoring the metabolic heterogeneity within a tumor by in vivo human spectroscopy. The clinical applications are not limited to these examples, but are mentioned in order to demonstrate that in vivo human spectroscopy has potential future clinical applications.

Today, the technology is still evolving. At this point, techniques must be developed to define the volume of interest (VOI) to ensure that the spectrum obtained is from the smallest region of interest and not from the surrounding tissue. Therefore, the technological challenge is to develop protocols which define controlled localized diseased areas, which will definitely have an impact on the early use of in vivo NMR spectroscopy as a routine clinical method for diagnostic purposes. In addition to the need for accuracy of localization, other desired features of an NMR spectrometer for clinical applications are to provide: 1) the best sensitivity per unit time, per unit volume; 2) the minimum of experimental time; and 3) ease of operation.

The identified needs of a MRS perfluorchemical are for it to be: 1) biocompatible and non-toxic; 2) having all fluorine atoms of equivalent magnetic resonance; 3) have a $T_1$ relaxation time highly responsive to dissolved oxygen and not paramagnetic ions; and 4) be cost effective.

Of the important nuclei in vivo spectroscopy, $^{31}P$ remains the most popular, since it offers a noninvasive, nondisruptive method for providing information on the vital role of phosphorous in many aspects of life processes. For example, $^{31}P$ NMR signals provide information on cellular energetics: phosphocreatine (PCr), adenosine triphosphate (ATP), and inorganic phosphate (Pi). ATP has been referred to as the "universal currency of free energy" in the human body, mainly because of its widespread use as a carrier of free energy within a cell. $^{31}P$ NMR also provides information concerning phospholipid syntheses and degradation, and also synthesis of glycoproteins/glycolipids. It also permits the measurement, invasively, of intracellular pH to indicate the acid/alkaline state of the tissue. These measurements are useful in understanding the state of health of tissues. Furthermore, the increase or decrease of $^{31}P$ resonance signal intensities of an intact tissue is useful in probing the biochemical and pathological aspects of diseased tissues. The changes in spectral patterns can be used to diagnose and monitor the treatment for a particular disease.

Parhamic and Fung established the characteristics of enhanced $^{19}F$ relaxation due to molecular oxygen and were one of the first to foresee the possibility of using $^{19}F$ NMR for in situ determination of the amount of oxygen dissolved in body fluids, organic or clinical studies. They investigated the current important fluorochemicals such as cis- and trans-perfluorodecalin and perfluorotributylamine. The logitudinal relaxation time ($1/T_1$) of each fluorine nuclei depended linearly on the partial pressure of oxygen. The slopes of their plots were different for each type of fluorine atom in the perfluorochemical. They reasoned steric effects rather than specific binding of molecular oxygen was the cause. P. Parhami and B. M. Fung, Fluorine-19 Relaxation Study of Perfluoro Chemicals as Oxygen Carriers, J. Physical Chemicals, 1983 pp 1928-1931.

Nunnally et al. showed that $^{19}F$-NMR spectra can be used to monitor the rate of blood pool and extravascular space dilution of a single bolus injection using emulsified fluorine species. Their data were the first results of in vivo $^{19}F$-NMR studies of perfusion and the determination of metabolism in specific organs using $^{19}F$-NMR. R. L. Nunnally, R. M. Peshock, R. B. Rehr, Fluorine-19 ($^{19}F$) NMR In Vivo. Potential For Flow And Perfusion o Measurements, Proceeding of the Society of Magnetic Resonance in Medicine, Second Annual Meeting Aug. 16-19, 1983 pg. 266.

In 1985 Reid et al. established that in a mixed fluorocarbon emulsion the spin-lattice relaxation rates of the component $^{19}F$ spectral lines were highly sensitive to oxygen concentration. R. S. Reid, C. J. Koch, M. E. Castro, E. O. Trisben, D. J. P. Boisvert and P. S. Allen. The Influence Of Oxygenation On The $^{19}$-Spin Lattice Relaxation Rates Of Fluosol DA, Phys. Med. Biol. Vol 30 No. 7, pp. 677-686 1985.

Wyrwicz et al. have shown that by using $^{19}F$-NMR spectroscopy they can detect small amounts (100-500 micromolar) of fluorinated anesthetics in the brain of live animals during and after anesthesia. A. M. Wyrwics, M. H. Pszenny, J. C. Schofield, R. E. Gordon and P. A. Martin, Observations Of Fluorinated Anesthetics In Rabbit Porain by $^{19}F$-NMR, Proceedings of the Society of Magnetic Resonance in Medicine, Second Annual Meeting, Aug. 16-19, 183 pp 381-382.

Clark, et al. showed, under their conditions, the $^{19}F$-NMR spectrum of perfluordecalin in emulsion, is not interfered with from liver tissue. They found that perfluorochemical $T_1$ relaxation times are insensitive to paramagnetic ions. L. C. Clark, J. L. Ackerman, S. R. Thomas, R. W. Millard, R. E. Hoffman, R. G. Pratt, H. Ragle-Cole, R. A. Kinsey and R. Janakiruman, Perfluorinated Organic Liquids And Emulsions As Biocompatible NMR Imaging Agents For $^{19}F$ And Dissolved Oxygen, Adv. Exp. Med. Biol. Vol. 180(6) pp 835-845, 1984.

The prior art, despite its suggestion for the use of magnetic resonance spectroscopy for medical and biodiagnostic purposes and the prior art's suggestion of various fluorine-containing compounds for use as agents in nuclear magnetic resonance spectroscopy, has failed to provide a particularly sensitive fluorine agent for nuclear magnetic resonance spectroscopy which provides high signal to noise ratios sufficient for detailed diagnosis of deep tissue structures and unexpectedly high and diagnostically useful NMR signal response to the presence to oxygen.

BRIEF SUMMARY OF THE INVENTION

The present invention is directed to a method for obtaining fluorine magnetic resonance spectra from body organs or tissues by administering to a mammal a fluorine-containing agent in a sufficient amount to provide one or more fluorine magnetic resonance spectra from said organs or tissues wherein the improvement comprises using as said fluorine-containing agent perfluoro 15-crown-5 ether.

Preferably, the perfluoro 15-crown-5 ether is administered in an aqueous isotonic emulsion with a fluorochemical concentration range of 5 to 25 wt %.

A particular embodiment of the present invention constitutes administering the perfluoro 15-crown-5 ether in emulsion form into body tissue for the purpose of quantifying the molecular oxygen concentration by measuring the absolute spin-lattice relaxation time ($T_1$).

Another embodiment of the present invention is the measurement of the rate of blood pool and extravascular space dilution by following the change in absolute intensity of the single sharp $^{19}F$-resonance line of perfluoro 15-crown-5 ether.

The perfluoro 15-crown-5 ether emulsion may be administered by a technique of direct injection into a body part, a body compartment, the bloodstream or by inhalation.

Alternatively, a method of the present invention can be performed by administering the perfluoro 15-crown-5 ether to a mammal, performing a biopsy of selected organ or body tissue and taking the $^{19}F$ spectrum of the biopsied tissue in vitro.

BRIEF DESCRIPTION OF THE DRAWINGS

FIG. 4 is an NMR spectrum of an equimolar concentration of perfluoro 15-crown-5 ether and perfluorodecalin showing that in comparison to the amplitude of the former, the latter appears as background noise response.

DETAILED DESCRIPTION OF THE INVENTION

Figure 1:
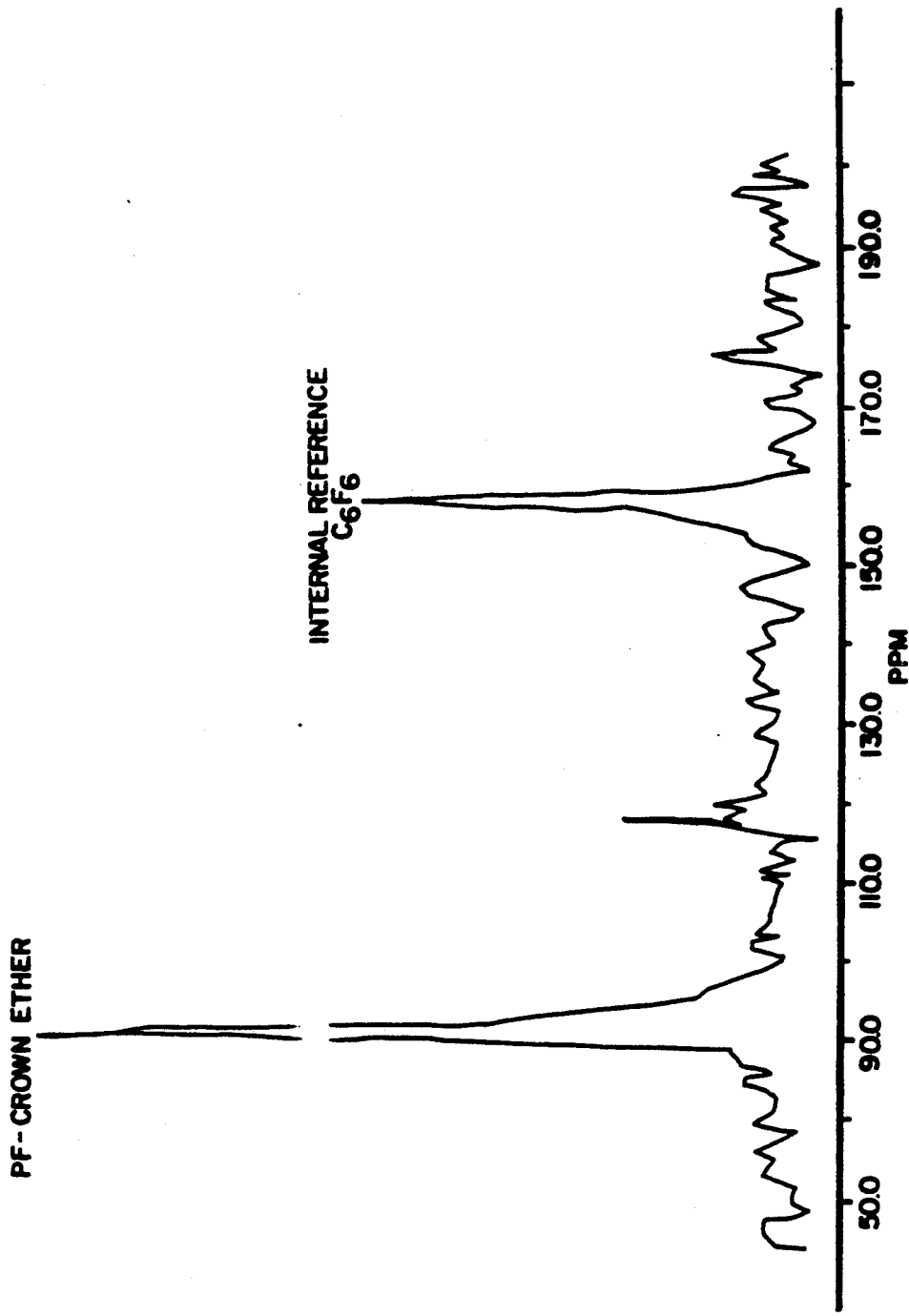
FIG. 1 is an NMR spectrum of perfluoro 15-crown-5 ether and a perfluorobenzene standard.

The present invention is directed to the field of spectroscopy, in contrast to the field of imaging which is disclosed in the present inventors' U.S. Pat. No. 4,838,274, hereby incorporated by reference herein in its entirety.

Fluorine atoms $^{19}F$ give a clear nuclear magnetic resonance signal and thus may function as suitable probes in nuclear magnetic resonance imaging and spectroscopy when combined in a chemically suitable form. The specific advantages flowing from the use of $^{19}F$ are:
(1) its low intrinsic concentration in soft tissues of the body;
(2) its high nuclear magnetic resonance sensitivity, and
(3) a magnetogyric ratio which is close to that of hydrogen, thereby making the observation of $^{19}F$ compatible with existing imaging and spectrographic devices.

However, the mere use of $^{19}F$ in various compounds does not provide the unexpected enhancement achieved by the present invention wherein the use of perfluoro 15-crown-5 ether provides the multiplied effect of 20 identically electronically and/or magnetically situated fluorine atoms. This particular chemical structure of fluorines provides a uniquely sharp signal when using nuclear magnetic resonance imaging in a biocompatible fluorine-containing agent. Perfluoro crown ethers have generally been recognized as having utility in biomedical applications. However, the present inventor has found that perfluoro 12-crown-4 ether is too volatile to be placed in the bloodstream of a mammal because of its tendency to form embolisms. On the other hand, perfluoro 18-crown-6 ether is too high in molecular weight for biomedical application, and despite its emulsification in a reasonably stable emulsion, when the agent is administered to a mammal, the ether precipitates out as a solid and shows marked toxicity.

Unexpectedly, perfluoro 15-crown-5 ether does not form embolisms and does not precipitate out of emulsion when administered to a mammal in an effective concentration sufficient for unexpectedly high signal to noise response ratios in magnetic resonance spectroscopy, particularly for diagnostic techniques for the determination of oxygen in organs, particularly the spaces surrounding and involved in tissue, tumors or cavities.

The unique location and association of fluorine atoms in perfluoro crown ethers provides the single sharp resonance line of maximum signal to noise ratio when used in magnetic resonance spectroscopy, because of the magnetic equivalence of all the fluorine nuclei. This provides the unique non-intrusive diagnostic capabilities of perfluoro crown ethers as a diagnostic technique.

The perfluoro 15-crown-5 ether emulsion form is useful for nuclear magnetic resonance diagnostic spectroscopy for diagnosis of tumors. The perfluoro 15-crown-5 ether is capable of highlighting specific biological dysfunctions. Additional diagnostic areas of interest include cardiovascular blood transport, which can be observed for site blockage, gastrointestinal constrictions which could be outlined, lung capacity and tissue degeneration could be located and tumor detection could be determined during early stages of tumor development due to the heightened sensitivity of the specific perfluoro crown ether.

The fluorine-containing agent of the present invention can be administered within an organ, tissue, space, blood vessel or cavity of a mammal. More specifically, the fluorine-containing agent of the present invention can be administered by a process selected from the group consisting of direct injection into a body part, direct injection into a body cavity (thoracic, peritoneal), direct injection into a body compartment (cerebrospinal fluid areas), direct injection into a space (subarachnoid), direct injection into a joint capsule, direct injection into the bloodstream, direct injection into a growth, tumor, lump or swollen tissue area.

After the administration of the agent to the mammal, the desired tissue can be biopsied and the biopsied and extracted tissue can be analyzed to give an $^{19}F$-NMR spectrum.

The $^{19}F$-magnetic resonance spectrum of the fluorine agent of the present invention can be used to monitor and quantify the oxygen tension of the subject tissue, organ, space or cavity by measurement of the spin-lattice (longitudinal) relaxation time ($1/T_1$).

The $^{19}F$-magnetic resonance spectrum of the fluorine agent of the present invention can be used for the identification of an isotense abnormal foci surrounded by normal tissue as a function of the oxygen tension in and around the abnormal foci.

The $^{19}$F-magnetic resonance spectrum of the fluorine agent of the present invention can also be used to monitor the rate of blood pool and extravascular space dilution of a single bolus injection.

Perfluoro 15-crown-5 ether was the only member of the perfluoro crown ether class of materials identified in U.S. Pat. No. 4,570,004 (hereby incorporated herein by reference) to form a stable aqueous emulsion at concentrations of 5 to 25 wt % in sterile saline with nonionic surfactant systems and also provide biocompatibility. This perfluoro crown ether was formulated into an appropriate emulsion as set forth in the following examples.

EXAMPLE 1

An emulsion of perfluoro 15-crown-5 ether (PF15C-5E) was prepared in sterile saline. One gram of perfluoro 15 crown-5 ether was sonicated for 5 minutes at 20° C. with 0.27 grams supercritically extracted egg yolk lecithin in 4.5 grams of normal saline.

EXAMPLE 2

In a typical control experiment, a normal, female Sprague-Dawley rat weighing approximately 290 grams, was anesthetized with ketamine hydrochloride. It was then injected directly into the fourth ventrile with five (5) microliter aliquots of the PF15C-5E emulsion (18 wt % fluorochemical) every five minutes until fifty microliters was injected. The animal was then isolated. The animal appeared normal and allowed to survive for 30 days. Gross examination did not reveal any irregularity. It was concluded that the fluorochemical emulsion was not toxic to the CNS (Central Nervous System). No trace of the fluorochemical was found in the animal after 30 days using capillary GC chromatography and an electron capture detector.

EXAMPLE 3

In a typical experiment, a normal female Sprague-Dawley rat weighing approximately 300 grams was anesthetized with ketamine hydrochloride. After sedation, the animal was injected into the fourth ventrile with five microliters of the perfluoro 15-crown-5 ether emulsion of Example 1 every five minutes until fifty microliters had been injected. After one hour and forty-five minutes an additional 0.13 cc of ketamine was injected to maintain a constant level of sedation during $^{19}$F-NMR spectroscopy.

The $^{19}$F magnetic resonance spectrum was taken on a 1.4K Tesla superconducting solenoid using a surface coil and time average computer techniques to collect the NMR spectra from the rat's brain. FIG. 1 gives the $^{19}$F magnetic resonance spectrum of perfluoro 15-crown-5 ether in aqueous emulsion from the brain of the rat. The reference signal of $C_6F_6$ was obtained by placing a capillary tube with $C_6F_6$ under the surface coil while the rat's brain was scanned.

EXAMPLE 4

In a typical experiment a Golden Hamster was injected into the femoral vein with 1 ml of the perfluoro 15-crown-5 ether of Example 1. The animal, after being injected with 0.22ml of Ketaset, was placed on its side on top of the NMR surface coil and a reference standard capillary, $C_6F_6$, placed underneath the animal. Spectra were taken with a Phosphoenergetrics 30 cm horizontal bore magnet operating at 2.2 Tesla. The resulting spectrum indicated that the perfluoro 15-crown-5 ether could be located within the animal's body near the location of the liver at the concentration of injection. The animal was sacrificed and its organs excised. Subsequent independent $^{19}$F magnetic resonance spectra were taken of each organ. The perfluoro 15-crown-5 ether was found in the spleen and liver confirming the in-vivo $^{19}$F NMR analysis.

EXAMPLE 5

The $^{19}$F magnetic resonance relaxation time $(1/T_j)$ of perfluoro 15-crown-5 ether was determined using a JEOL FX90Q spectrometer. A perfluoro 15-crown-5 ether emulsion was prepared as in Example 1. The stock emulsion was separated equally into three (3) NMR tubes into which the oxygen concentration was established to be zero, 18% and 100%, respectively. The NMR spectrum of each sample was taken at 37° C. The relaxation time, $1/T_1$, of the NMR signal was found to change from 0.5 sec-1 to 0.87 sec-1 to 2.9 sec-1 with increasing partial pressure of oxygen. These in vitro measurements of the spin lattice relaxation times $(1/T_1)$ were found to compare with the in vivo measurement of $1/T_1$ in hamsters, which were administered comparably oxygenated emulsions, to give an estimate of the oxygen tension of the diagnosed tissue of the hamsters with good experimentally correlated accuracy.

Figure 2:
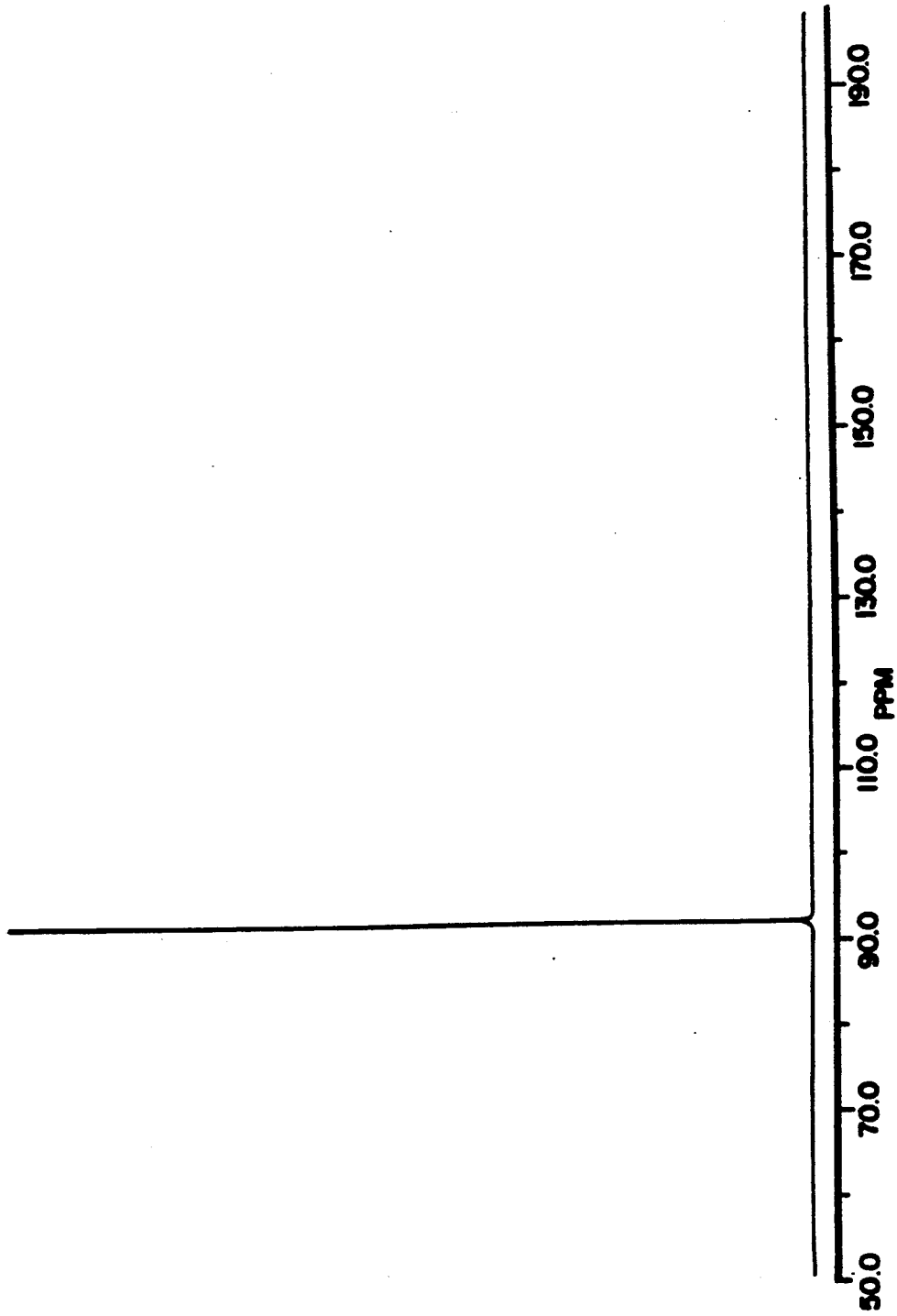
FIG. 2 is an NMR spectrum of perfluoro 15-crown-5 ether taken alone to shown the clean single response peak.
Figure 3:
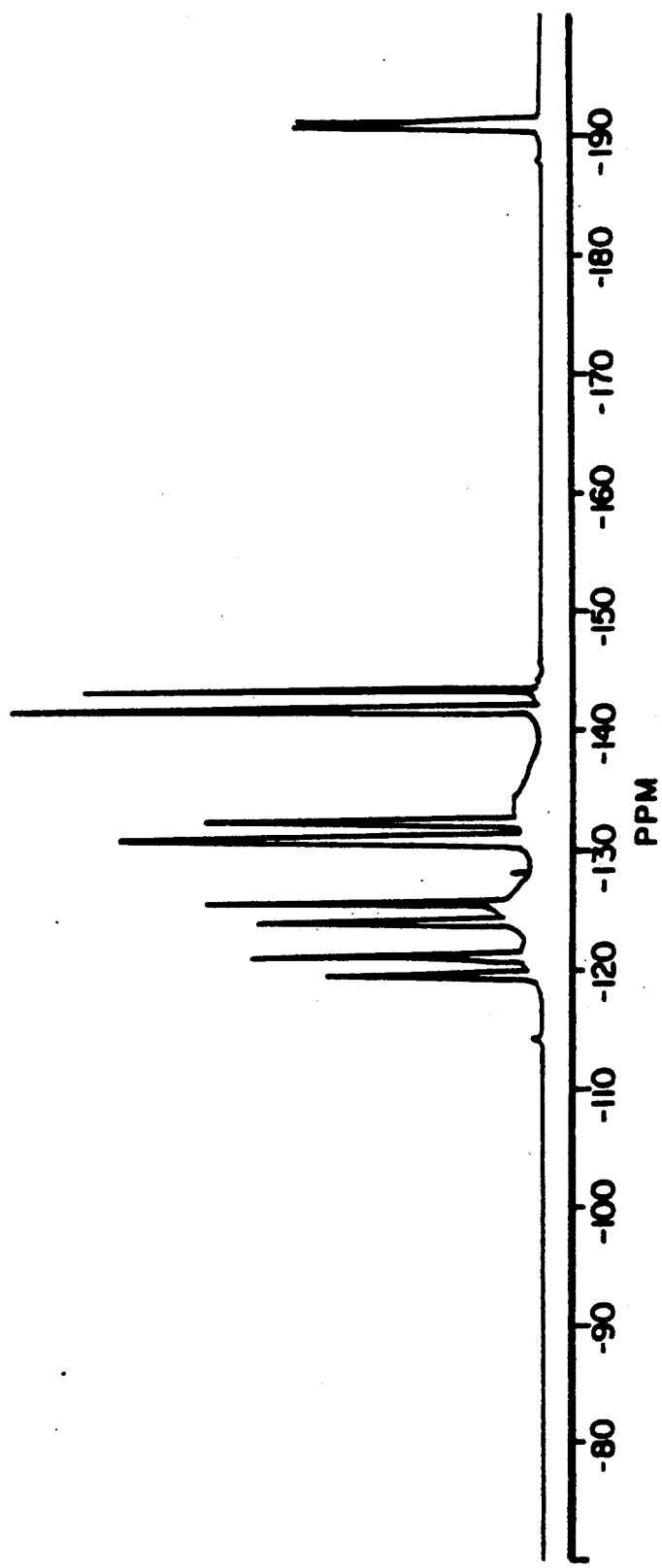
FIG. 3 is an NMR spectrum of perfluorodecalin taken alone to show the multitude of response peaks which it gives as the state of the art.

The advantage to using perfluoro 15-crown-5 ether is that the compound's $^{19}$F-NMR spectrum consists of a single sharp line, FIG. 2, while the present state of the art uses perfluorochemicals that give multiple peaks, such as perfluorodecalin, FIG. 3. The single peak of perfluoro 15-crown-5 ether represents 20 magnetically equivalent fluorines. Because of the 20 equivalent fluorines, the relative sensitivity in the NMR of PF-15-crown-5 ether is five times greater than any other bio-acceptable perfluoro-compound, see FIG. 4 for a comparison between perfluoro-15-crown-5 ether and perfluorodecalin.

The disadvantage using compounds with more than one peak is selecting which peak to monitor during the in vivo or in vitro diagnostic analysis. If low field strength ($<1.4$ Tesla) magnets are used the resolution of peaks is greatly diminished. This effect causes the peaks of nearly equivalent nuclei (their chemical shift) to coalesce into a broad unresolved peak. Because each equivalent nuclei will respond to the presence of oxygen with a slightly different relaxation time $(1/T_1)$, the final information is comprised and of less diagnostic value. Higher field magnets ($>1.8$ Tesla) can separate some of the chemical shifts. Larger magnets are limited with today's technology to the size of the magnet bore, thus reducing the size of the subject to be examined. Perfluoro 15-crown-ether emulsions allow for a broader range of application, contribute the greatest sensitivity per volume of agent injected and directly yield the desired oxygen tension information about the tissue or organ under evaluation without applying mathematical conversions to the data.

The perfluoro-15-crown-5 ether emulsion is the ideal chemical answer to a problem that has been addressed with mechanical and mathematical approaches for the past 10 years, that is, how to isolate a single $^{19}$F-NMR resonance for in vivo diagnostic applications.

The present invention has been set forth with emphasis of a particular preferred embodiment. However, the scope of the present invention should be ascertained from the claims which follow.

We claim:

1. In a method of obtaining a $^{19}$F-fluorine magnetic resonance spectrum from body organs or tissue by administering to a mammal a fluorine-containing agent in a diagnostically effective amount to provide a fluorine magnetic resonance spectrum from such organs or tissues, the improvement comprising using as said fluorine-containing agent an aqueous isotonic emulsion of perfluoro 15-crown-5 ether and after the administration of the agent to the mammal, the desired tissue is biopsied and the biopsied and extracted tissue is analyzed to give an $^{19}$F-fluorine magnetic resonance spectrum.

2. The method of claim 1 where in the concentration of the emulsion is the range of 5 to 25 wt % of the perfluoro 15-crown-5 ether.

3. The method of claim 1 wherein said fluorine-containing agent is administered within an organ, tissue, space, blood vessel or cavity of a mammal.

4. The method of claim 1 wherein the fluorine-containing agent is administered by a process selected from the group consisting of direct injection into a body organ, direct injection into a body cavity, direct injection into a tissue area.

* * * * *